(12) United States Patent
Palmer

(10) Patent No.: US 11,771,868 B2
(45) Date of Patent: *Oct. 3, 2023

(54) GRIPPER SLEEVE FOR URINARY CATHETER

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/239,080

(22) Filed: Apr. 23, 2021

(65) Prior Publication Data

US 2021/0338979 A1 Nov. 4, 2021

Related U.S. Application Data

(63) Continuation of application No. 16/861,941, filed on Apr. 29, 2020, now Pat. No. 10,987,487.

(51) Int. Cl.
*A61M 25/01* (2006.01)

(52) U.S. Cl.
CPC ..... *A61M 25/01* (2013.01); *A61M 2202/0496* (2013.01)

(58) Field of Classification Search
CPC .......... A61M 25/01; A61M 2202/0496; A61M 25/002
USPC ........................................ 604/544, 265, 172
See application file for complete search history.

(56) References Cited

U.S. PATENT DOCUMENTS

| 3,421,509 A * | 1/1969 | Fiore ................. A61M 25/0119 604/171 |
| 3,683,928 A | 8/1972 | Kuntz |
| 7,476,223 B2 * | 1/2009 | McBride ............. A61M 25/002 206/210 |
| 9,884,167 B2 | 2/2018 | Gustavsson |
| 10,099,032 B2 | 10/2018 | Gustavsson et al. |
| 10,646,688 B2 * | 5/2020 | Hannon ............. A61M 25/0017 |
| 2012/0141049 A1 * | 6/2012 | Paulin .................... B65D 31/12 383/64 |
| 2014/0066904 A1 * | 3/2014 | Young ................ A61M 25/0111 604/544 |
| 2015/0273183 A1 * | 10/2015 | Foley ................ A61M 25/0021 604/544 |

(Continued)

OTHER PUBLICATIONS

"Cure medical introduces the pediatric Hydrophilic Cure Catheter" Aug. 17, 2017 (Year: 2017).*

(Continued)

*Primary Examiner* — Nicholas J. Weiss
*Assistant Examiner* — Gabriella E Burnette
(74) *Attorney, Agent, or Firm* — SoCal IP Law Group LLP; Guy Cumberbatch; Steven C. Sereboff

(57) ABSTRACT

An enhanced tubular sleeve for handling a urinary catheter including a number of features that render usage of urinary catheters much easier and reduce discomfort. The sleeve may be formed of bonded sheets of flexible material having rounded distal ends. Or, the sheets may only be bonded in a proximal portion with their distal portions left unattached. In still another version the distal end of one sheet terminates shorter than the distal end of the other sheet.

20 Claims, 8 Drawing Sheets

(56) References Cited

U.S. PATENT DOCUMENTS

2015/0343171 A1* 12/2015 Hannon ............. A61M 25/0111
604/544

OTHER PUBLICATIONS

Wayback Machine "The Hyrdophilic Cure Catheter for men" Feb. 3, 2018 (Year: 2018).*

World Intellectual Property Organization, International Search Report and Written Opinion for International Application No. PCT/US2021/027517, dated Jul. 29, 2012, pp. 1-10.

A youtube video of the product "Hydrophilic Cure Catheter® for men" available at (https:// www.youtube.com/watch?v=K5VbHvYoj9k) The product description is disclosed in the application Cure Medical, LLC Jun. 11, 2018 (Jun. 11, 2018) 0:16 and 0:40 on the youttube video; Para. [0032], [0036]-[0038] and Figs. 1-2 in the application descriptio.

"Cure medical introduces the pediatric Hydrophilic Cure Catheter", last accessed Aug. 17, 2017.

Wayback Machine, "The Hydrophilic Cure Catheter for Men", last accessed Feb. 3, 2018.

* cited by examiner

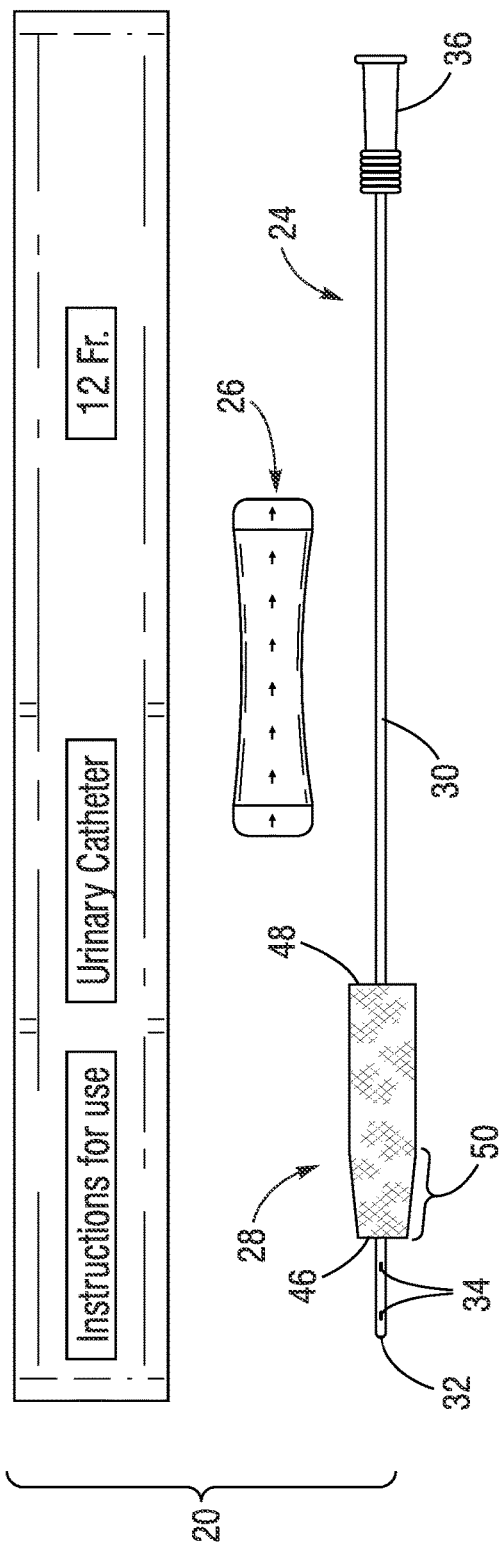
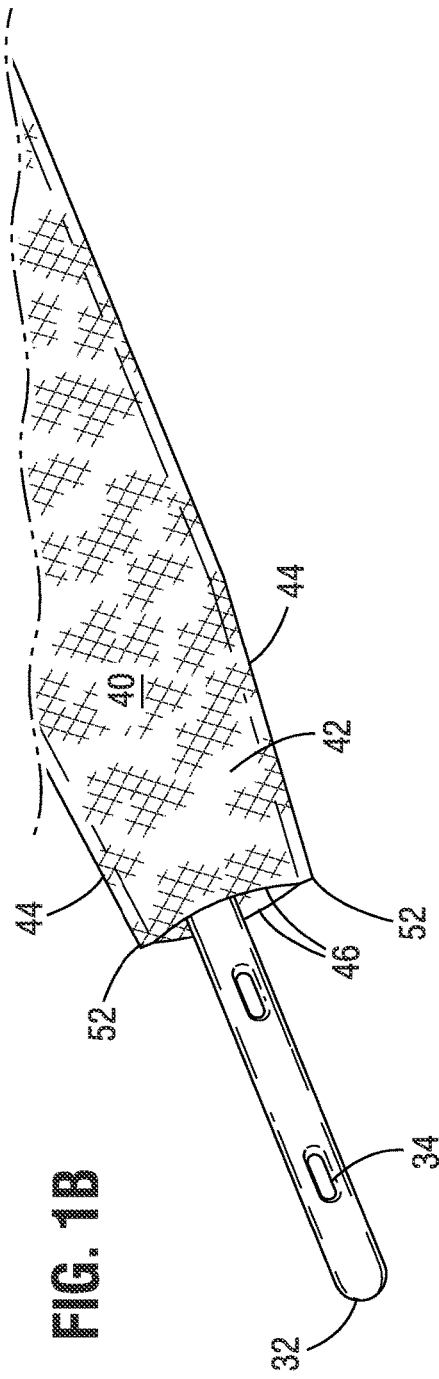
FIG. 1A (Prior Art)
FIG. 1B

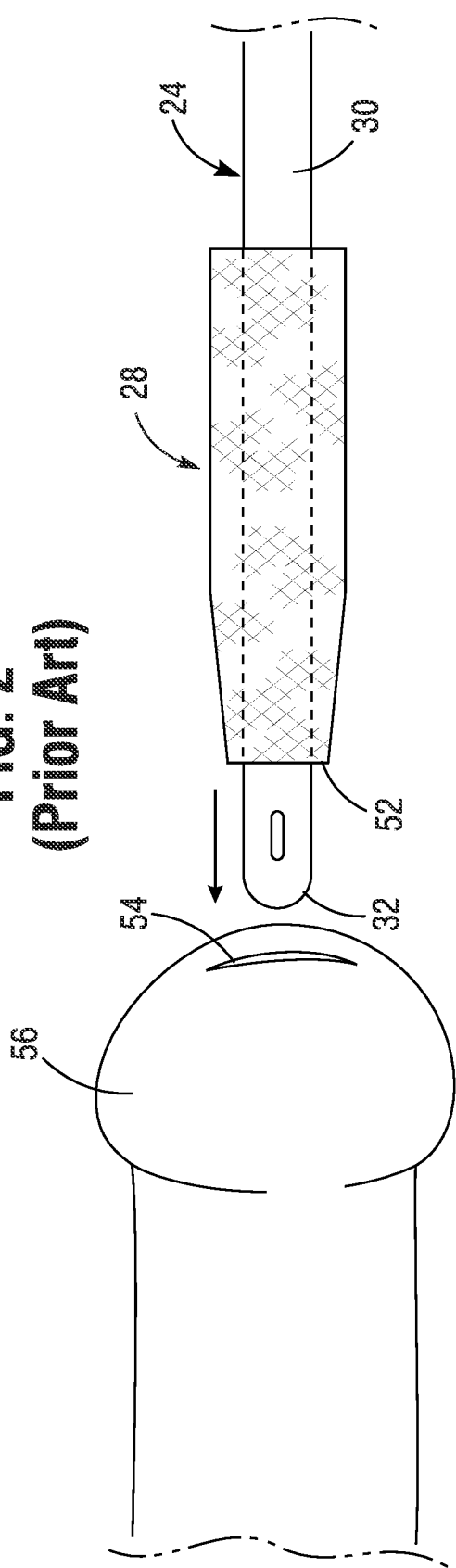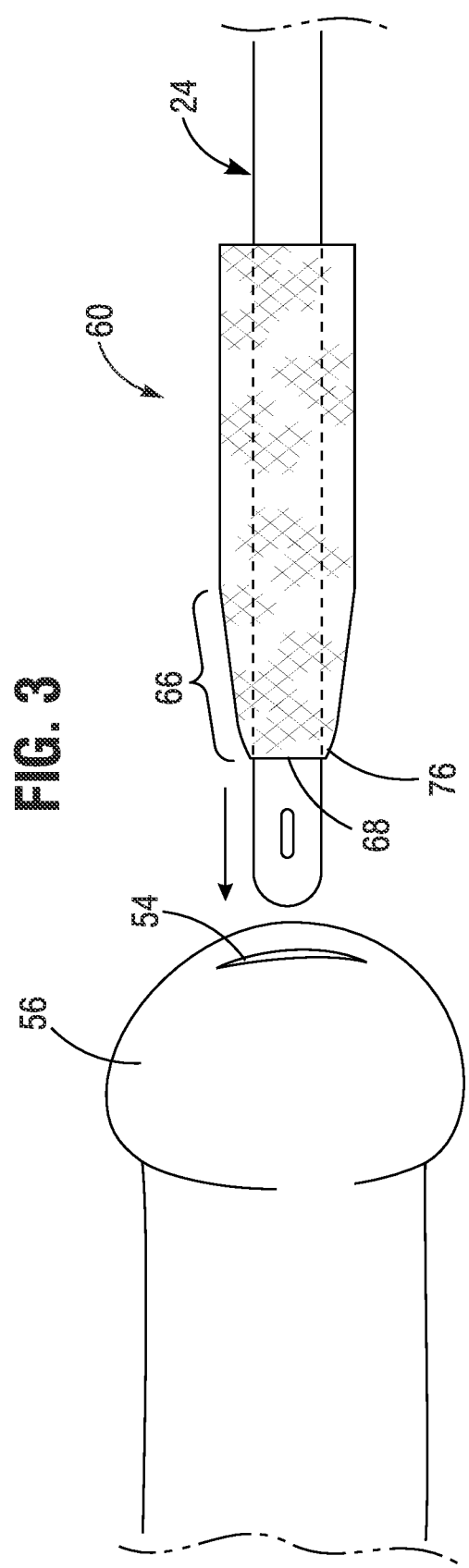

GRIPPER SLEEVE FOR URINARY CATHETER

RELATED APPLICATIONS

The present application is a continuation of U.S. patent application Ser. No. 16/861,941, filed Apr. 29, 2020, the contents of which are expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner have no objection to the facsimile reproduction by anyone of the patent disclosure as it appears in the Patent and Trademark Office patent files or records, but otherwise reserves all copyright and trade dress rights whatsoever.

FIELD

The present application relates to an intermittent urinary catheter and, more particularly, to an improved gripping sleeve used to manually advance a lubricated intermittent urinary catheter.

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need, single use catheters have been developed to allow patients to perform self-catheterization, and are termed intermittent urinary catheters.

Most intermittent urinary catheters are lubricated in some manner to facilitate introduction to and advancement through the urethra. The two main techniques of lubrication are automatically or manually applying a gel to the exterior of the catheter, or breaking a water sachet within the sealed catheter package to activate a hydrophilic surface coating on the catheter. Hydrophilic catheters have a polymer coating that binds to the surface of the catheter. When the polymer coating is submersed in water, it absorbs and binds the water to the catheter, which becomes smooth and very slippery.

Whichever way the catheter is lubricated, it becomes slick and difficult to handle once removed from the package. The rounded tip of the catheter must be inserted into the urethra, and often the users of intermittent catheters have limited dexterity. For example, spinal injuries leading to partial paralysis of the limbs, and limited use of fingers, sometimes also results in the need for urinary catheters. The process for manipulating a urinary catheter is somewhat difficult, especially in light of the need to maintain sterility, which makes gripping and inserting a lubricated catheter into the urethra extremely hard even for fully functioning users.

Various solutions to this problem have been developed in the art. For example, U.S. Pat. No. 9,884,127 to Gustaysson discloses an elastomeric tubular insertion aid that fits over the catheter and has an external ribs so as to be used as a handle to move the catheter back and forth without touching it (e.g., see FIG. 3b). The insertion aid slides back and forth on the catheter while the patient inches the catheter forward. However, this molded design is relatively complex and thus prohibitively expensive for a product which is used multiple times a day and disposable.

U.S. Pat. No. 7,476,223 issued to McBride discloses another urinary catheter set having a tubular cuff 40 disposed so as to be movable along the length of the catheter (see FIG. 2). The cuff 40 is a flat-compressed plastic sheeting tube, tapered on the front end, with welded longitudinal edges, much like construction of a plastic bag. This has the advantage of low manufacturing costs and a low profile which facilitates storage inside the package. However, the cuff 40 sometimes creates discomfort, especially in male users, which limits widespread adoption.

Though a number of solutions for manually manipulating hydrophilic urinary catheters are known in the art, there remains a need for a more comfortable and thus accepted gripping cuff or sleeve.

SUMMARY OF THE INVENTION

Embodiments of the present invention seek to provide an enhanced sleeve for handling a urinary catheter. The present application provides a number of features that render usage of urinary catheters much easier, and in particular reduce discomfort.

In one embodiment, a sleeve for handling a urinary catheter, comprises a pair of flexible flat sheets of material that each have proximal and distal ends defining a longitudinal axis therebetween and are bonded together at longitudinal edges to form a sleeve which may be expanded into a tubular shape sized to loosely receive a urinary catheter. The sheets of material each having a rectangular proximal portion extending from the proximal end, and a tapered distal portion terminating at the distal end. The tapered distal portion of each sheet includes an elongated constantly tapered section that transitions to a rounded portion just before the distal end.

Both sheets of material may be identical, or the sheets of material have different lengths or the sheets may be offset with respect to each other with the distal end of a first sheet terminating shorter than the distal end of a second sheet. For instance, the distal end of the first sheet terminates 1-3 mm shorter than the distal end of the second sheet. The sheets of material are desirably bonded at longitudinal edges along the proximal portions, while at least some of the tapered distal portions including the distal ends are not bonded. In one configuration, the entire distal ends of each of the sheets of material are rounded with no discrete corners. Preferably, the sheets of material each have textured inner or outer surfaces.

Another embodiment of a sleeve for handling a urinary catheter includes a pair of flexible flat sheets of material that each have proximal and distal ends defining a longitudinal axis therebetween and are bonded together at parallel longitudinal edges to form a sleeve which may be expanded into a tubular shape sized to loosely receive a urinary catheter. The sheets of material are bonded at longitudinal edges along proximal portions, while at least some of the distal portions including the distal ends are not bonded. The sheets of material may have a rectangular proximal portion extending from the proximal end, and a tapered distal portion terminating at the distal end.

A still further embodiment of a sleeve for handling a urinary catheter includes a pair of flexible flat sheets of material that each have proximal and distal ends defining a longitudinal axis therebetween and are bonded together at longitudinal edges to form a sleeve which may be expanded into a tubular shape sized to loosely receive a urinary catheter. The sheets of material have different lengths or offsetting ends with the distal end of a first sheet terminating shorter than the distal end of a second sheet. The sheets of material may have a rectangular proximal portion extending from the proximal end, and a tapered distal portion terminating at the distal end.

BRIEF DESCRIPTION OF THE DRAWINGS

FIG. 1A is an exploded view of a prior art intermittent urinary catheter package assembly, including outer packaging, a catheter with a gripping sleeve, and a water sachet;

FIG. 1B is an enlarged perspective view of a distal end of the prior art urinary catheter with the gripping sleeve thereon;

FIG. 2 illustrates advancement of the prior art urinary catheter and gripping sleeve just prior to insertion into the external urethral opening of a male;

FIG. 3 illustrates advancement of a urinary catheter and gripping sleeve of the present application toward the external urethral opening of a male;

DETAILED DESCRIPTION OF A PREFERRED EMBODIMENT

Figure 4:
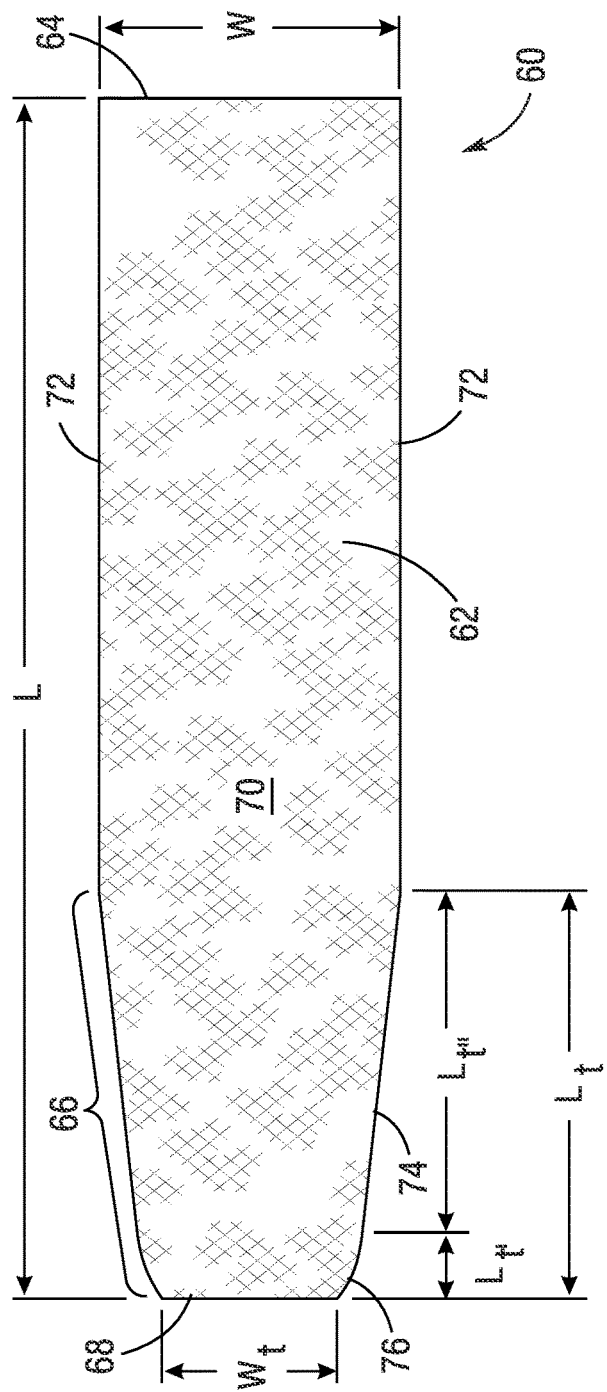
FIG. 4 is a top plan view of an exemplary gripping sleeve such as shown in use in FIG. 3.

The present application provides an improved gripping cuff or sleeve for use with intermittent urinary catheters. Hydrophilic catheters often use a sleeve-like gripping device to assist users to feed the catheter once the hydrophilic coating is hydrated and slippery. The user typically grasps the catheter tube using the gripping device and is then able to push the catheter forward to insert it into the urethra. This provides greater friction and avoids the mess inherited touching a lubricated catheter. Moreover, the gripping device provides a sanitary barrier between the user's hand and the catheter to help avoid transferring bacteria to the urethra, which might lead to infection.

As mentioned in the background, existing catheter handling or gripping cuffs or sleeves can create discomfort. Specifically, some patients complain that sharp corners of the front of the gripping sleeve are irritating to the patient skin when they come into contact with the skin. The improved gripping sleeve described herein are particularly beneficial for catheters designed for males, but it should be understood that the same principles can just as easily be incorporated into a catheter for use by females.

FIG. 1A illustrates a prior art intermittent urinary catheter package assembly 20 exploded, including outer packaging 22, a catheter 24 with a gripping sleeve 28 slidable thereover, and a water sachet 26. When packaged, the catheter 24 with gripping sleeve 28 along with water sachet 26 are contained in a sterile manner within the outer packaging 22. In the illustrated embodiment, the prior art urinary catheter package assembly 20 is the Hydrophilic Cure Catheter® for men available from Cure Medical, LLC, of Newport Beach, Calif.

The outer packaging 22 of the Hydrophilic Cure Catheter® for men is a simple tubular sleeve of flexible water-impermeable material, such as thin polyethylene. In a preferred embodiment, a front face of the outer packaging 22, shown in FIG. 1A, is opaque and has a number of markings thereon, such as the product enclosed, instructions for use, and the size (e.g., 12 Fr). A rear face (not shown) may be transparent so that the contents can be easily viewed. Catheters for men typically range between 12-18 inches long, and the outer packaging 22 is thus slightly longer.

The catheter 24 shown in FIG. 1A has a catheter tube 30 with a polymeric hydrophilic coating on its exterior that terminates at a front or distal end in a rounded distal tip 32. One or more drainage openings 34 are formed adjacent the rounded distal tip 32. An elastomeric funnel 36 attaches to a rear or proximal end of the catheter tube 30.

In use, prior to opening the sterile packaging 22, the user squeezes or bends the water sachet 26 which is filled with purified water causing the sachet to burst and distribute the water within the package and around the catheter tube 30. This activates the hydrophilic coating on the catheter tube 30, thus rendering it lubricious. The user opens the sterile packaging 22, typically by tearing apart the two sheets of material that form the front and rear faces, much like opening a Band-Aid. The user can handle the catheter 24 at the funnel 36, which is not slippery, as well as by grasping the gripping sleeve 28 which is typically conveniently positioned near the distal end of the catheter tube 30. Manipulation of the catheter tube 30, and in particular by aiming the distal tip 32, the catheter can be inserted into the urethra.

FIG. 1B is an enlarged perspective view of the distal end of the prior art urinary catheter 24 with the gripping sleeve 28 on the catheter tube 30. The gripping sleeve 28 of the Hydrophilic Cure Catheter® for men has a textured inner surface 40 which enhances the frictional qualities and thus the user's grip. The two drainage openings 34 are shown axially spaced apart adjacent the distal tip 32. In a preferred embodiment, the drainage openings 34 have rounded edges that are recessed into the wall of the catheter tube 30 for greater comfort to the user.

The construction of the gripping sleeve 28 is illustrated clearly in FIG. 1B. In particular, the sleeve comprises two identical flat sheets of flexible material 42 that are bonded (e.g., heat welded) together along the entirety of their juxtaposed longitudinal edges 44. The sheets of flexible material 42 remain disconnected at front and rear ends 46, 48 of the sleeve 28 to form tubular shape sized to loosely receive a urinary catheter 24 for sliding movement therethrough. The gripping sleeve 28 further includes a slightly narrowing tapered section 50 toward the front end 46, but otherwise has a constant lateral dimension, as seen best in FIG. 1A.

The enlargement of FIG. 1B illustrates the welded seams formed along the juxtaposed longitudinal edges 44. These seams terminate at the front end 46 of the gripping sleeve 28 in relatively sharp corners 52. These corners 52 tend to create discomfort for the patient if they come in contact with the outer opening of the urethra, as will be described below.

FIG. 2 illustrates advancement of the prior art urinary catheter 24 and gripping sleeve 28 just prior to insertion into the external urethral opening 54 of a male penis 56. Typically, the user will hold with one hand the gripping sleeve 28 to maneuver the distal catheter tip 32 close to the urethral opening 54, and then advance the catheter tube 30 using the other hand typically holding the rear funnel 36 (FIG. 1A). The process of aiming the distal tip 32 to successfully enter the urethral opening 54 requires the user to bring the gripping sleeve 28 holding the tip into close proximity with the opening. Some patients have complained that the sharp corners 52 of the front of the sleeve 28 are irritating to the patient's skin when they come into contact with the skin; often times this is the meatus of the user's penis 56 which is a sensitive area. The sharp corners 52 are reinforced by the stiffness of the welded sides 44 extending to the distal end of the sleeve 28. After several times experiencing such discomfort, the natural behavioral result is a much more careful and thus time-consuming catheterization process. In extreme cases the user may choose to not use the sleeve and touch the catheter with their bare hand.

To alleviate this discomfort, and facilitate the process, the present application presents a number of different catheter gripping sleeves which have a front-end that eliminates any sharp corners, and in some cases are more flexible than the prior sleeve.

For instance, FIG. 3 illustrates advancement of a urinary catheter 24 and gripping sleeve 60 of the present application toward the external urethral opening 54 of a male. The urinary catheter 24 is desirably constructed the same as in the prior art, and thus like elements will be given like numbers.

FIG. 4 is a top plan view of an exemplary gripping sleeve 60 which includes a generally tubular body 62 extending from a proximal end 64 to a tapered portion 66 adjacent a distal end 68. As before, the tubular body 62 is desirably formed of a pair of identical flexible strips of material, such as polyethylene, with a textured inner or outer surface 70 to increase friction. The texturing may be on the inner or outer surfaces of the sheets, and conceivably on the inside of one and the outside of the other. Ideally the texturing would be on both the inner and outer surfaces, but manufacturing constraints limit it to one or the other. The texturing is typically formed by a heated knurled or cross-hatched roller on one side of a large blank of material which is then cut to size and shape for the sheets to form each side of the tubular body 62. Alternatively, two blanks are bonded together, before or after forming the individual sleeve sheets, and texturing added on the outside of both, which is a more efficient process.

Juxtaposed longitudinal edges 72 of the strips are bonded together, such as with heat welding, to form the sleeve 60 which may be expanded into the tubular body 62 sized to loosely receive a urinary catheter. As will be explained below, the entire length of the adjacent longitudinal edges 72 may be bonded, or only the parallel, longitudinal portions may be bonded with some or all of the distal tapered portion 66 remaining unattached. It should also be noted that the distal tapered portion 66 includes an elongated constantly tapered section 74 transitions to a shorter rounded portion 76 that terminates at the laterally-oriented distal end 68.

With reference to FIG. 3, advancement of the catheter 24 using the gripping sleeve 60 occurs as usual. Should the user bring the gripping sleeve 60 into contact with the penis 56 in this process, the distal end 68 and the relatively shallow corners leading to the rounded portion 76 will be the first to touch. Due to the elimination of the sharp 90° corners 52 in the prior art sleeves, the discomfort to the user is greatly reduced. Specifically, the intersection of the rounded portions 76 with the laterally-oriented distal end 68 may form corners having a 60° included angle or less. Furthermore, and as will be clear in certain embodiments below, the sleeves that make up the tubular body 62 of the sleeve 60 may be left unattached in the tapered portion 66. This eliminates the bonded seams that would have extended to the distal end 68, leaving two relatively flexible flaps which easily bend, and which the user will not feel.

With reference back to FIG. 4, certain exemplary dimensions are provided. As will be understood, these dimensions are guidelines only, are provided to indicate relative sizes, and may vary by up to 20% each. An exemplary total length L is 80±5 mm, and an exemplary total width W is 22±1 at the proximal end 64. The length $L_t$ of the tapered portion 66 is desirably between 30-40% of the total length L, for example 27 mm. For instance, the short rounded portion 76 may have a length $L_{t'}$ of 7 mm, and the longer gradually tapered portion 74 may have a length $L_{t''}$ of 20 mm. The width $W_t$ at the narrow end of the tapered portion 66 is desirably between 55-75% of the total width, for example 13-15 mm.

Figure 5:
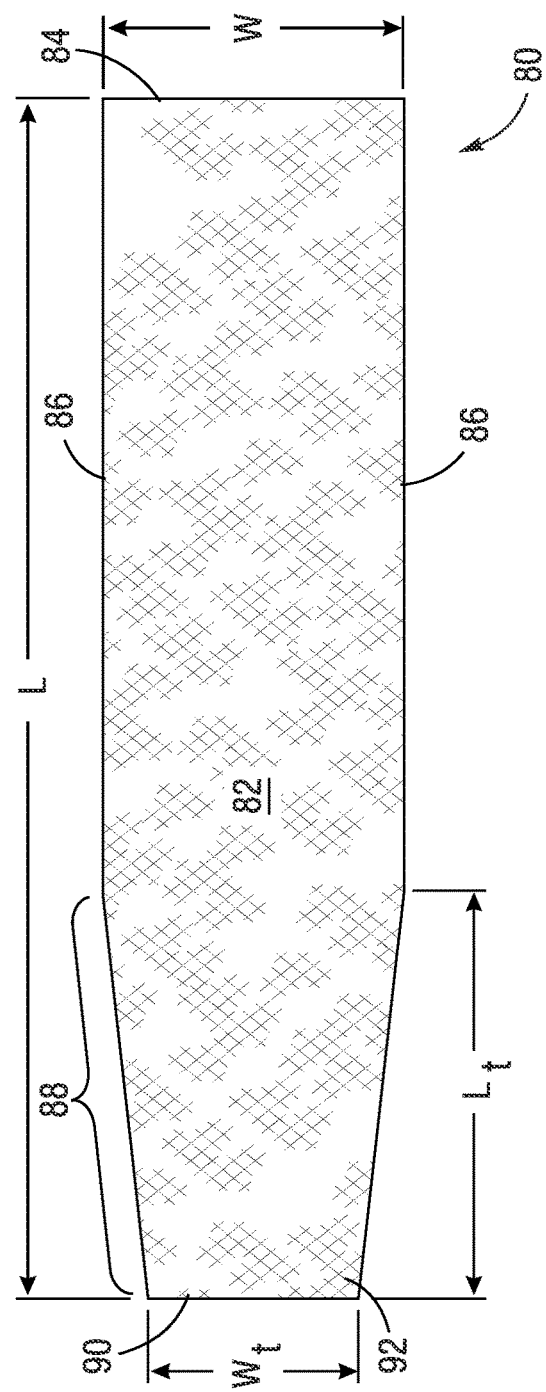
FIG. 5 is a top plan view of a second embodiment of a gripping sleeve of the present application.

FIG. 5 is a top plan view of a second embodiment of a gripping sleeve 80 of the present application. This gripping sleeve 80 has a shape identical to the prior art gripping sleeve 28, with a proximal portion 82 commencing at a proximal end 84 having sides 86 that are parallel and longitudinally-oriented, and a distal tapered portion 88 terminating at a distal end 90. In this embodiment, the distal tapered portion 88 has a constant narrow taper out to the distal end 90. Although the intersection of the distal tapered portion 88 and the distal end 90 forms sharp corners 92, the two strips of material that comprise the gripping sleeve 80 are only bonded together along the sides 86 in the proximal portion 82, but remain detached in the distal tapered portion 88. It should be noted that the lack of bonding may not be along the whole length of the tapered portion 88 as long as at least about 1-3 mm is detached adjacent the distal end 90.

This leaves two relatively loose flaps at the distal end 90, which easily bend and create no discomfort to the male user if they contact the penis 56, for example. Once again, the benefits of the improved gripping sleeves described herein are equally realized when incorporated into a catheter for use by females.

Figure 6A:
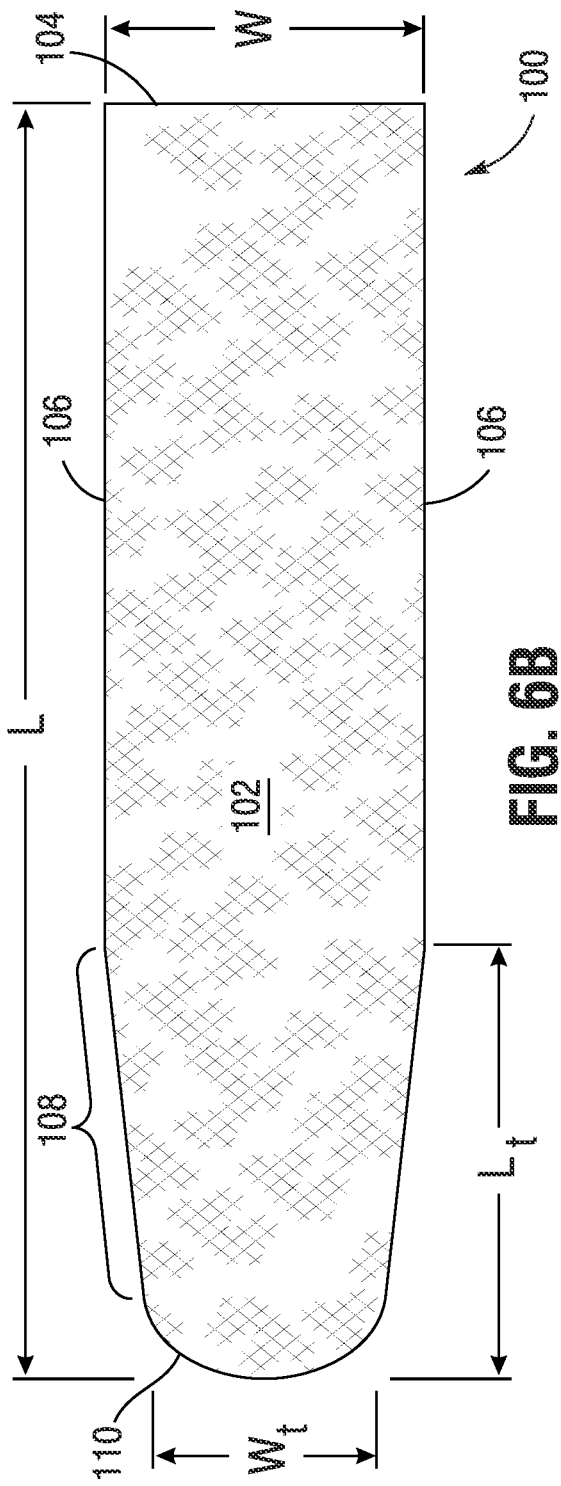
FIG. 6A is a top plan view of a third embodiment of a gripping sleeve of the present application.
Figure 6B:
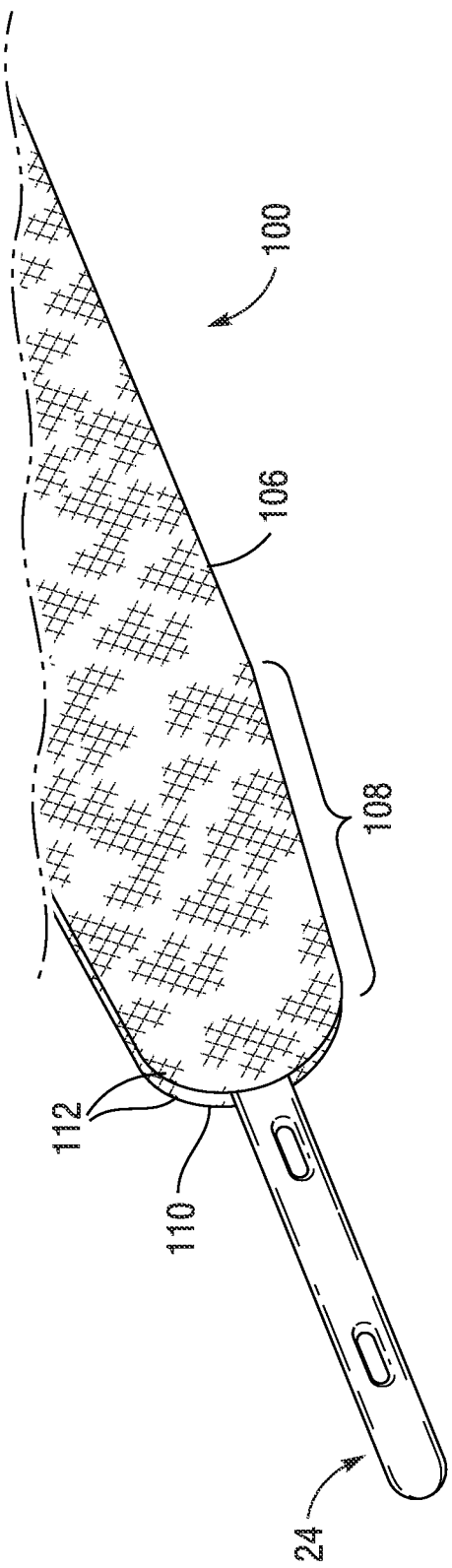
FIG. 6B is a perspective view of the gripping sleeve surrounding a urinary catheter.

FIG. 6A is a top plan view of a third embodiment of a gripping sleeve 100 of the present application, and FIG. 6B is a perspective view of the gripping sleeve surrounding a urinary catheter 24. Much like the previous gripping sleeve, the gripping sleeve 100 is formed by the attachment of two strips of flexible material connected together in a tubular fashion and have a proximal portion 102 commencing at a proximal end 104 having sides 106 that are parallel and longitudinally-oriented, and a distal tapered portion 108 terminating at a distal end 110. In contrast to the earlier embodiment, the entire distal end 110 is rounded from the end of the tapered portion 108 on either side. This alleviates any discrete corners whatsoever and greatly reduces patient discomfort from inadvertent contact between the sleeve 100 and the area surrounding the urethral opening 54.

With reference to FIG. 6B, the sleeve 100 is shown near the distal end of the catheter 24. In this version, the distal portion of the sleeve 100 including the tapered portion 108 and distal end 110 are detached from one another, thus forming two loose flaps 112. As explained above, the strips of material are only bonded together at seams along the sides 106 that are parallel and longitudinally oriented. The two loose flaps 112 at the distal end 110 thus present almost no structural resistance and attendant discomfort if they inadvertently come in contact with the user's penis 56.

Figure 7A:
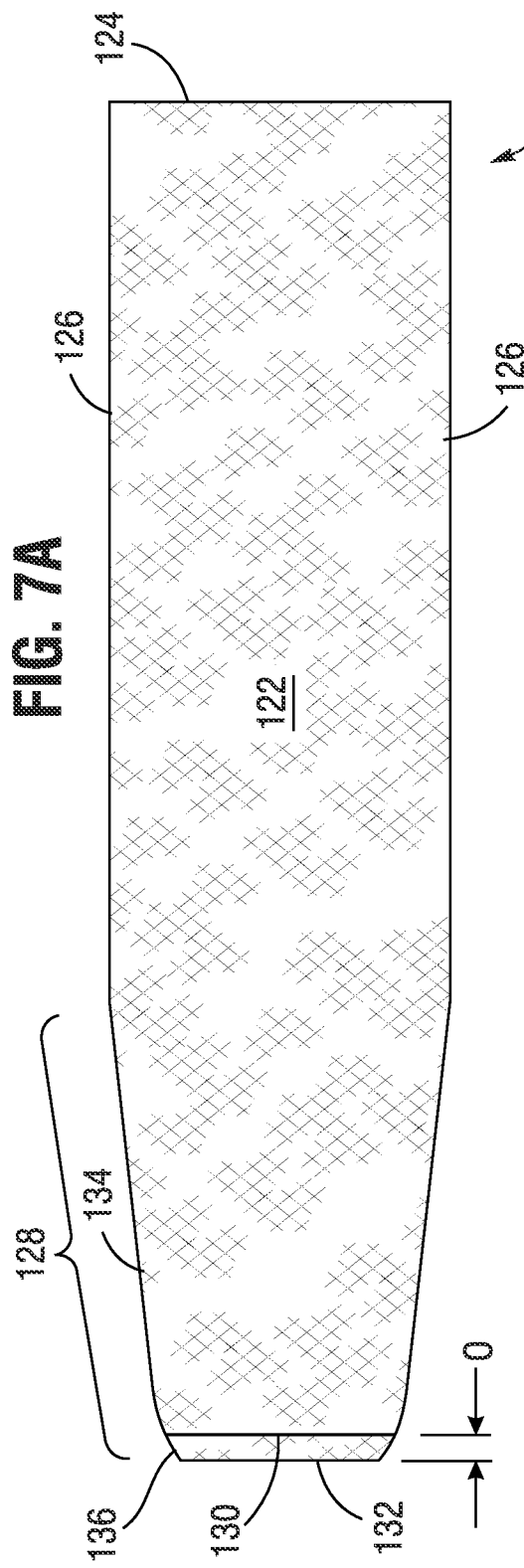
FIG. 7A is a top plan view of a fourth embodiment of a gripping sleeve of the present application.

FIG. 7A is a top plan view of a fourth embodiment of a gripping sleeve 120 of the present application. As before, the gripping sleeve 120 comprises two strips of flexible material connected together in a tubular fashion to form a proximal portion 122 commencing at a proximal end 124 having sides 126 that are parallel and longitudinally-oriented, and a distal tapered portion 128. In contrast with the earlier embodiment, the two strips of flexible material may not be identical, with a first strip being shorter than a second strip such that a first distal end 130 terminates short of a second distal end 132. Alternatively, the strips could be the same size but offset at each end.

For instance, the first distal end 130 terminates short of the second distal end 132 by 1-3 mm, preferably 2 mm. In the illustrated embodiment, the first strip is positioned on top of the second strip, though this arrangement could be reversed. The distal tapered portion 128 is shaped similar to that in the gripping sleeve 60 shown in FIG. 4, with an elongated constantly tapered section 134 leading to a shorter rounded portion 136 that terminates at the distal ends 130, 132. The two strips of material that form the gripping sleeve 120 are desirably not connected along their sides 126 along the distal tapered portion 120, though as explained below they may alternatively be welded.

Figure 7B:
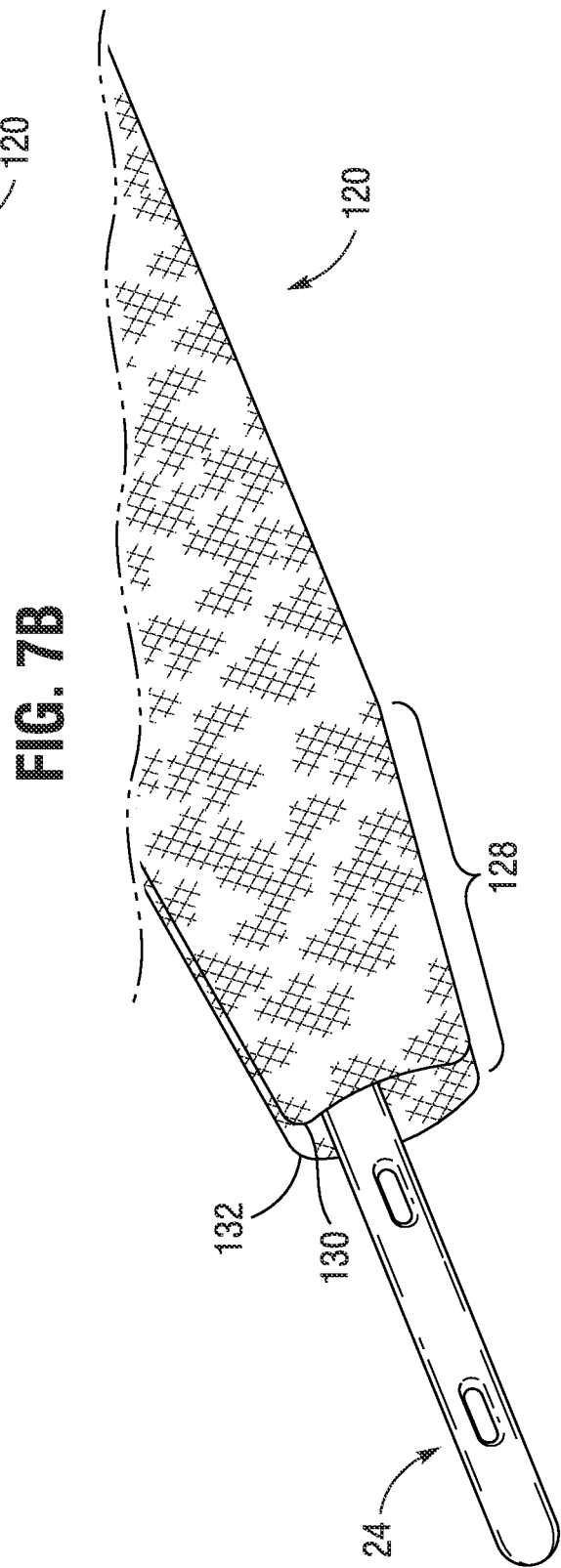
FIG. 7B is a perspective view of the gripping sleeve surrounding a urinary catheter.

FIG. 7B is a perspective view of the gripping sleeve 120 surrounding a urinary catheter 24. It is readily apparent that the distal end of the sleeve 120 forms two separated flaps terminating at the two distal ends 130, 132. Due to the extremely flexible nature of the separated flaps and the shape of the sleeve at the distal ends 130, 132, the user will experience almost no structural resistance if the sleeve 120 inadvertently contacts the penis during use. Only one thin sheet of soft, flexible material can touch the user.

In the prior art sleeve, the weld line between the 2 sheets formed a sharp corner, yet even if the two sheets shown in FIGS. 7A/7B remain welded together, the offset ends 130, 132 eliminate the weld in that area. That is, the juxtaposed edges of the two strips of flexible material may be bonded up to the termination of the shorter distal end 130. In addition, the tapering plus semi-rounded front contour further acts to deflect forces. In still another embodiment, not shown, the sleeve 120 may have a straight (constant) taper in the distal tapered portion 128 without the rounded portion 136, and be bonded up to the termination of the shorter distal end 130. Even though the distal corners of the second distal end 132 are sharp, the lack of a bond between the two sheets at the distal corners reduces the stiffness considerably.

Another aspect of the present application is a provision of two gripping sleeves for one catheter package. Having two gripping sleeves enables the user to "inchworm" the catheter into the urethra. The two sleeves can be brought close together to meet up, then the catheter is advanced by gripping and moving one while letting the catheter slide through the other. This provides an advantage over simply gripping and pushing the catheter from the proximal funnel.

Figure 8A:
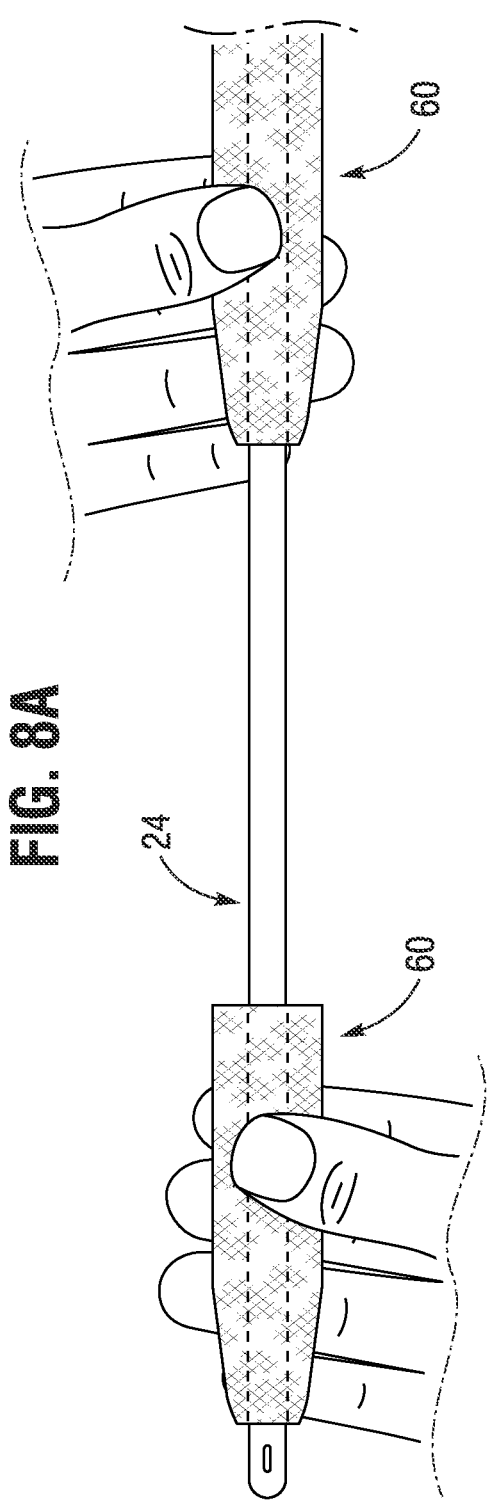
FIGS. 8A and 8B illustrate a urinary catheter having two gripping sleeves thereon in use.
Figure 8B:
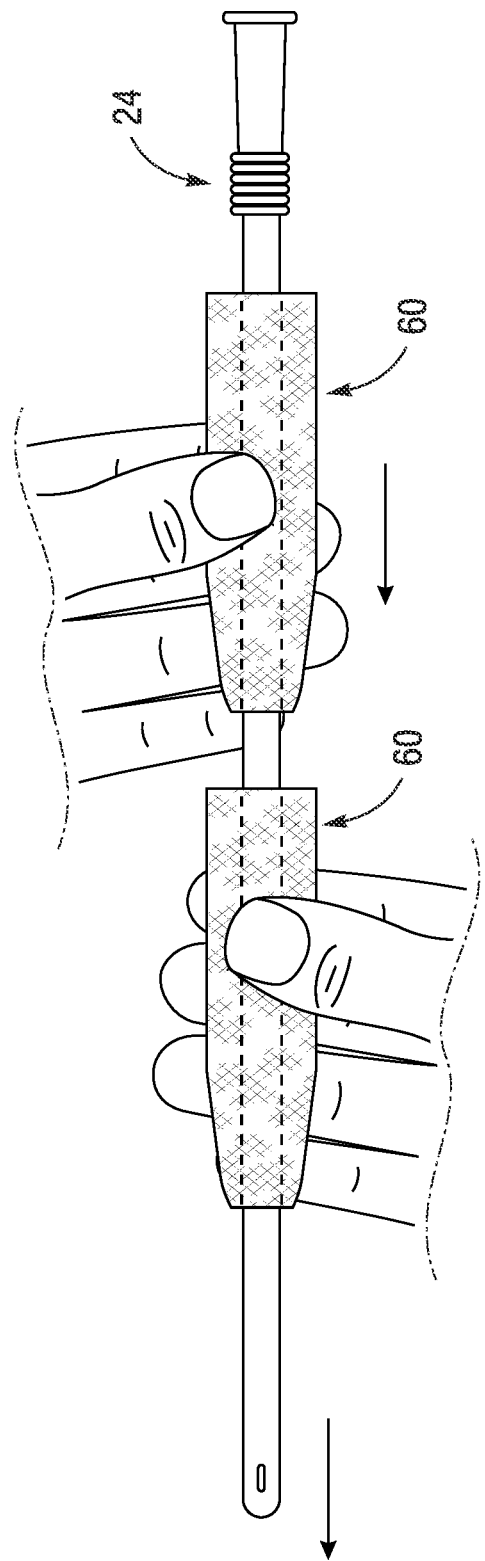

FIGS. 8A and 8B illustrate a urinary catheter 24 having two gripping sleeves 60 thereon in use. In these illustrations, the gripping sleeves 60 are configured like the gripping sleeve 60 shown and described with respect to FIGS. 3-4. Initially, the user grasps the forward sleeve 60 with the first hand close to the distal tip of the catheter 24, and grasps the rearward sleeve 60 with the second hand at a distance therefrom. FIG. 8B shows advancement of the second hand relative to the first hand and forward sleeve to advance the catheter 24. Although not shown, the user then holds the forward sleeve 60 while sliding the rearward sleeve back on the catheter for further movement.

Figure 9:
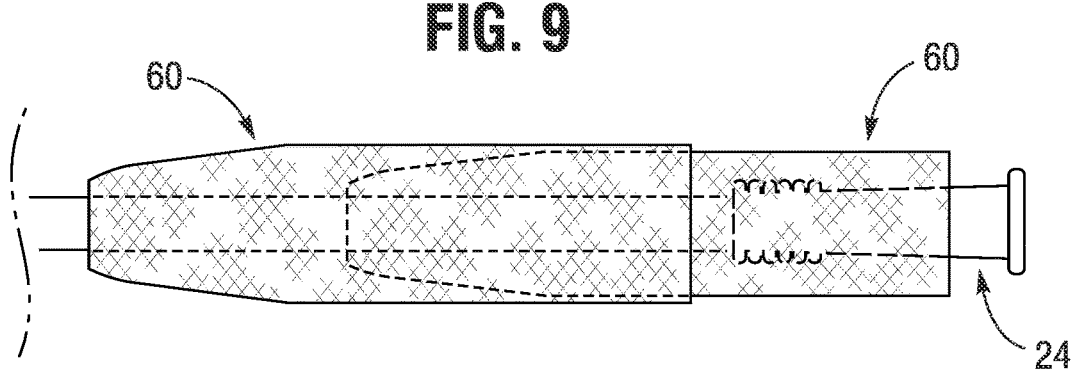
FIG. 9 illustrates an exemplary configuration of two gripping sleeves nested over a urinary catheter for shipping.

FIG. 9 illustrates an exemplary configuration of two gripping sleeves 60 nested over a urinary catheter 24 for shipping. That is, a rearward sleeve can be slid over the proximal funnel of the catheter 24, and the forward sleeve slid partially over the rearward sleeve. This conveniently positions the two sleeves 60 at a clean (i.e., non-lubricated) end of the catheter 24 for ease-of-use.

Figure 10A:
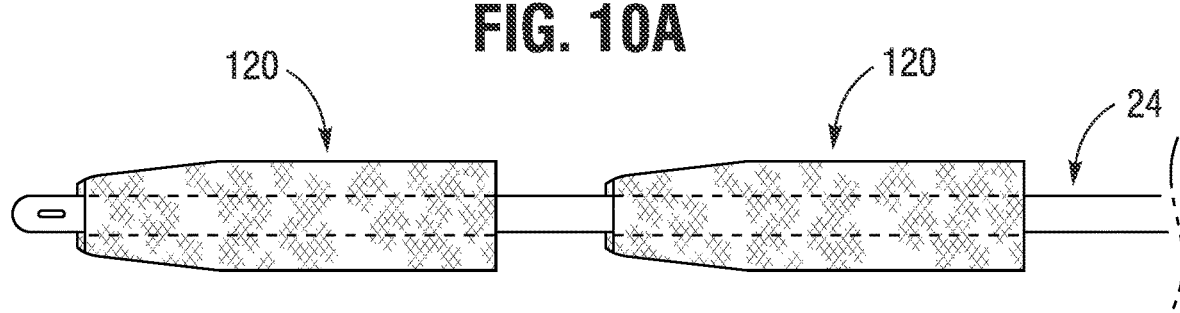
FIGS. 10A-10C are alternative combinations of dual gripping sleeves on urinary catheters.
Figure 10B:
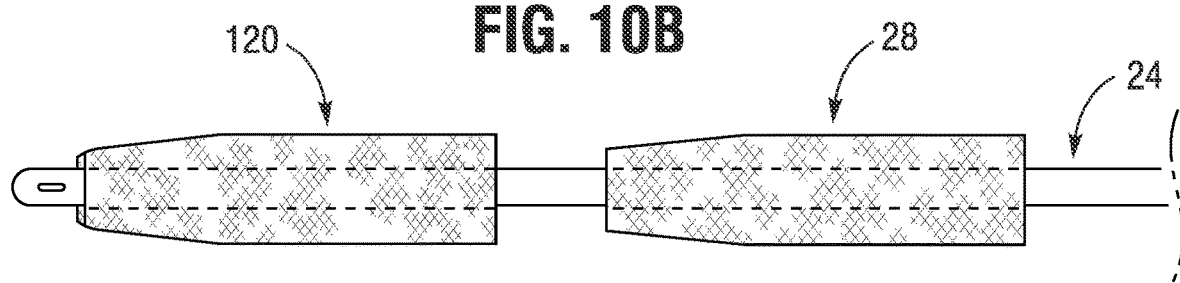
Figure 10C:
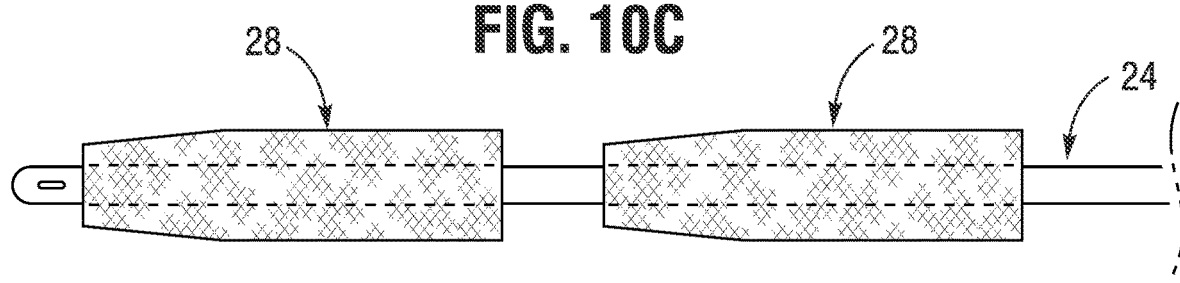

FIGS. 10A-10C are alternative combinations of dual gripping sleeves on urinary catheters to illustrate several possible permutations. In the first embodiment of FIG. 10A, the two sleeves 120 are identical; in this case the sleeve shown and described with respect to FIGS. 7A and 7B. In FIG. 10B, the sleeves are different, with the sleeve 120 of the present application on the forward end, with a prior art sleeve 28 on the rearward end. Because the forward sleeve 120 is the one that will potentially contact the user, the benefits of enhanced comfort are provided, and it is irrelevant what form the rear sleeve 28 takes. Finally, FIG. 10C is a version with two of the prior art sleeves 28 on the catheter 24. Although this embodiment will not provide the comfort of the improved gripping sleeve described herein, it is included to show that the advantages of having two gripping sleeves on one catheter are present even with the earlier sleeves.

FIGS. 11A-11F are top plan views of alternative shapes and configurations of exemplary gripping sleeves. The standard shape for gripping sleeves in the urinary catheter field is as shown in FIG. 1A, which has a proximal rectangular section and the tapered distal section 50. The tapered distal section 50 is provided to prevent the gripping sleeve 28 from sliding completely over the proximal funnel 36 to keep the assembly together. However, other shapes for the gripping sleeves are possible.

Figure 11A:
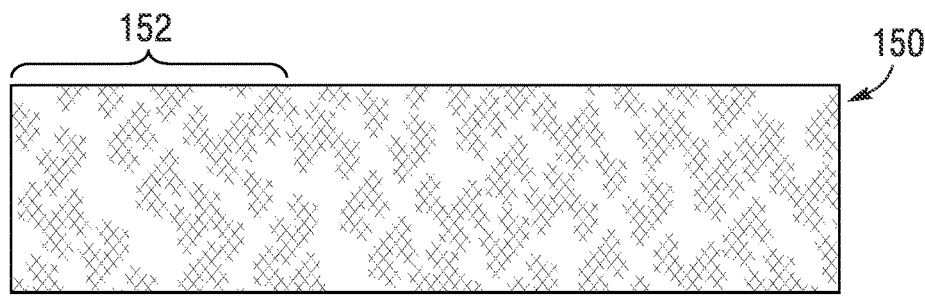
FIGS. 11A-11F are top plan views of alternative shapes and configurations of exemplary gripping sleeves.

For example, FIG. 11A illustrates a gripping sleeve 150 formed by the juxtaposition of two identical rectangular sheets of flexible material, preferably textured on the inside. The longitudinal sides of the sheets of material are bonded together except at a distal or forward portion 152, which as explained above, can be as small as 1-3 mm long. Because the two sheets of material are not bonded at the distal end, they do not present a sharp bonded corner which can cause irritation to the patient.

Figure 11B:
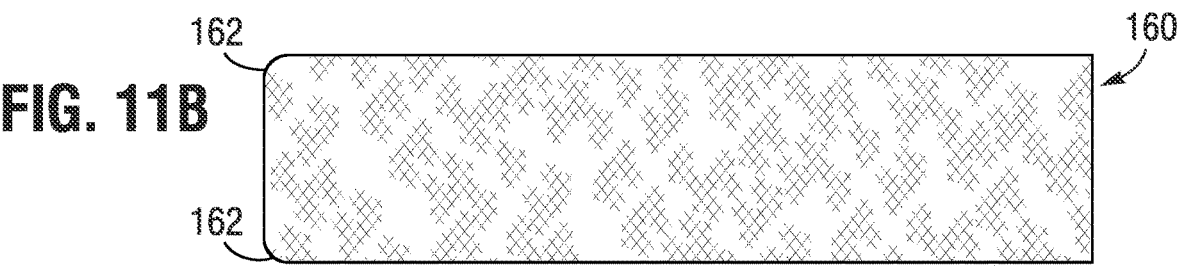

FIG. 11B illustrates another generally rectangular gripping sleeve 160 formed with two sheets of flexible material that are bonded along the longitudinal side edges. As with certain embodiments described above, distal corners 162 of the gripping sleeve 160 are rounded. The rounded corners 162 may be bonded together, or the two sheets may be bonded along their straight longitudinal edges all the way up to the beginning of the curvature of the rounded corners and 60.

Figure 11C:
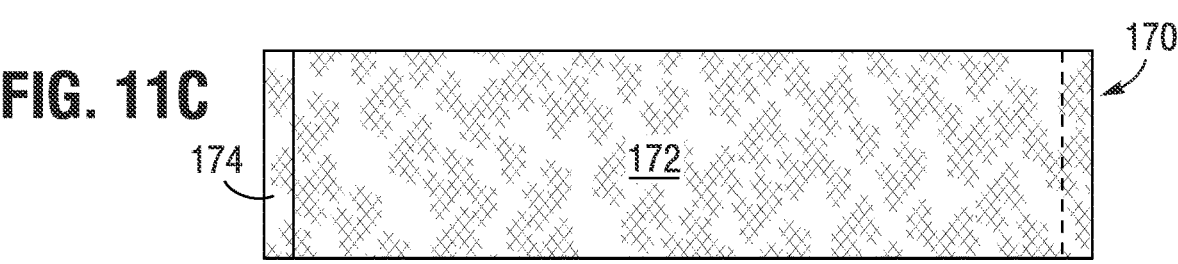

FIG. 11C shows a still further rectangular gripping sleeve 170 formed by two offset sheets of flexible material bonded together along their longitudinal side edges. A top sheet 172 is offset in a proximal direction over a bottom sheet 174. This leaves a short distance of just the bottom sheet 174 at the distal end of the gripping sleeve 170, which presents highly flexible and thus non-irritating distal corners to the user.

Figure 11D:
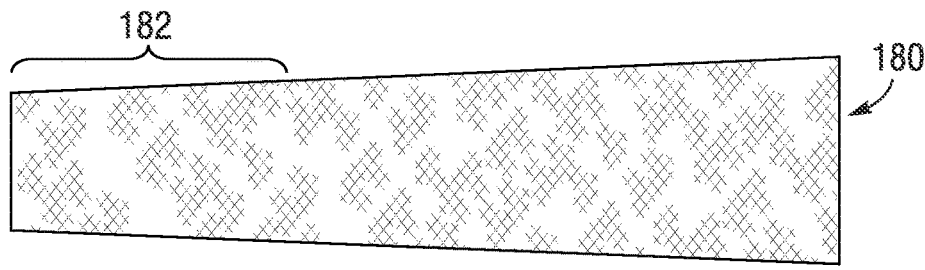

FIG. 11D shows a fully tapered gripping sleeve 180 that has a larger width at its proximal end of its distal formed by two identical sheets of flexible material bonded together along part of their long straight side edges. Much like the gripping sleeve 150 in FIG. 11A, the side edges along a distal or forward portion 182 remain unattached to avoid the sharp bonded corners that cause discomfort to the patient.

Figure 11E:
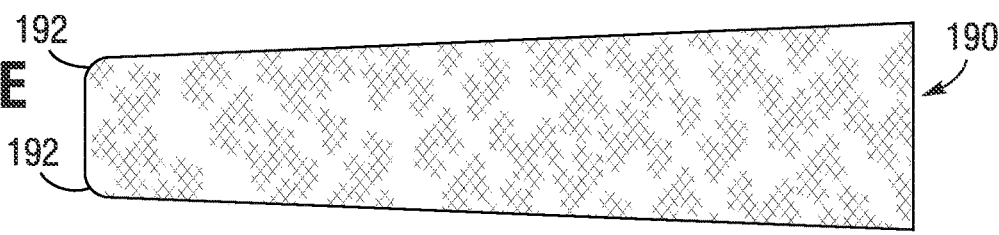

FIG. 11E shows another fully tapered gripping sleeve 190 formed by identical sheets of flexible material that are larger on their proximal ends and the distal ends. Distal corners 192 are again rounded to reduce discomfort to the patient. As before, the corners 192 may be bonded or not.

Figure 11F:
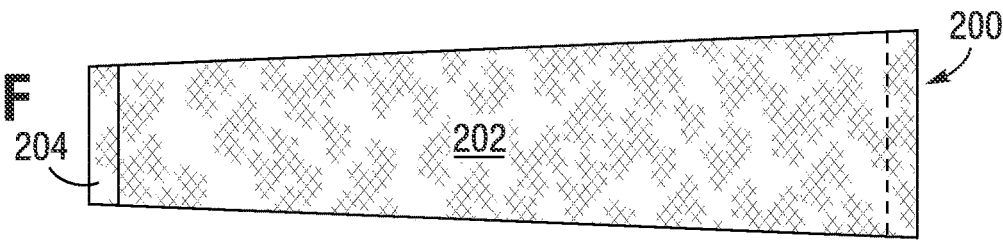

Finally, FIG. 11F shows another fully tapered gripping sleeve 200 with offset flexible sheath bonded together. A top sheet 202 is offset in a proximal direction over the bottom sheet 204. The two sheets 202, 204 are bonded together along their juxtaposed straight side edges. A small portion of the bottom sheet 204 extends forward as shown and presents very soft and pliable distal corners which reduce irritation to the user.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A gripping sleeve for handling a urinary catheter, comprising:
    a pair of flexible flat sheets of material having textured inner or outer surfaces that each have proximal and distal ends defining a longitudinal axis therebetween and are bonded together at longitudinal edges to form a sleeve which may be expanded into a tubular shape sized to loosely receive a urinary catheter such that the catheter passes loosely through open proximal and distal ends, wherein the sheets of material are bonded along proximal portions of the longitudinal edges, while at least some of the distal portions of the longitudinal edges all the way to the distal ends are not bonded to result in two separated flaps, the distal ends being laterally-oriented perpendicular to the longitudinal axis, the sleeve being configured to loosely surround the urinary catheter for sliding movement of the urinary catheter therethrough and to assist a user in handling the urinary catheter.

2. The gripping sleeve of claim 1, wherein the sheets of material are both rectangular.

3. The gripping sleeve of claim 1, wherein both sheets of material are at least partly tapered narrower in a proximal-distal direction.

4. The gripping sleeve of claim 3, wherein the proximal portion of both sheets of material have a rectangular shape extending from the proximal end, and the distal portion of both sheets of material are tapered and terminate at the distal end.

5. The gripping sleeve of claim 4, wherein the tapered distal portion of each sheet includes a constantly tapered section leading to a rounded portion just before the distal end.

6. The gripping sleeve of claim 4, wherein the tapered distal portion of each sheet is constantly tapered from the proximal portion to the distal end.

7. The gripping sleeve of claim 1, wherein the sheets of material both narrow on a constant taper from the proximal to the distal ends.

8. The gripping sleeve of claim 1, wherein the distal end of a first sheet terminates shorter than the distal end of a second sheet.

9. The gripping sleeve of claim 8, wherein the longitudinal edges transition to rounded portions just before the distal ends.

10. The gripping sleeve of claim 1, wherein the entire distal ends of each of the sheets of material are rounded with no discrete corners.

11. A gripping sleeve for handling a urinary catheter, comprising:
    a pair of flexible flat sheets of material having textured inner or outer surfaces that each have proximal and distal ends defining a longitudinal axis therebetween and are bonded together at juxtaposed longitudinal edges to form a sleeve which may be expanded into a tubular shape sized to loosely receive a urinary catheter such that the catheter passes loosely through open proximal and distal ends, the distal ends being laterally-oriented perpendicular to the longitudinal axis and having a length sufficient such that when expanded into a tubular shape the catheter may easily slide therethrough, wherein the longitudinal edges transition to rounded portions just before the distal ends, the sleeve being configured to loosely surround the urinary catheter for sliding movement of the urinary catheter therethrough and to assist a user in handling the urinary catheter.

12. The gripping sleeve of claim 11, wherein the sheets of material are both rectangular except at the rounded portions.

13. The gripping sleeve of claim 11, wherein both sheets of material are at least partly tapered narrower in a proximal-distal direction.

14. The gripping sleeve of claim 13, wherein the proximal portion of both sheets of material have a rectangular shape extending from the proximal end, and the distal portion of both sheets of material are tapered and terminate at the rounded portions.

15. The gripping sleeve of claim 11, wherein the sheets of material both narrow on a constant taper from the proximal to the distal ends and terminate at the rounded portions.

16. The gripping sleeve of claim 11, wherein the entire distal ends of each of the sheets of material are rounded with no discrete corners.

17. The gripping sleeve of claim 11, wherein the distal end of a first sheet terminates shorter than the distal end of a second sheet to form offset distal ends.

18. The gripping sleeve of claim 17, wherein the distal end of the first sheet terminates 1-3 mm shorter than the distal end of the second sheet.

19. The gripping sleeve of claim 17, wherein at least some of the distal portions of the longitudinal edges all the way to the distal ends are not bonded to result in two separated flaps.

20. The gripping sleeve of claim 17, wherein the two sheets have identical lengths such that the proximal end of the first sheet is also longitudinally offset from the proximal end of the second sheet.

\* \* \* \* \*